United States Patent [19]

Zhu et al.

[11] Patent Number: 5,545,302

[45] Date of Patent: Aug. 13, 1996

[54] SUPPRESSION OF ELECTROENDOSMOSIS DURING ELECTROPHORESIS IN GEL-FREE POLYMER MEDIA BY USE OF CHARGED POLYMERS

[75] Inventors: Ming-De Zhu; Christopher J. Siebert, both of Berkeley, Calif.

[73] Assignee: Bio-Rad Laboratories, Inc., Hercules, Calif.

[21] Appl. No.: 411,613

[22] Filed: Apr. 5, 1995

Related U.S. Application Data

[63] Continuation-in-part of Ser. No. 136,689, Oct. 14, 1993, abandoned.

[51] Int. Cl.$^6$ .......................... G01N 27/26; G01N 27/447
[52] U.S. Cl. ........................... 204/454; 204/451; 204/601
[58] Field of Search ............................ 204/180.1, 182.8, 204/299 R

[56] References Cited

U.S. PATENT DOCUMENTS 5,264,101  11/1993  Demorest et al. .................. 204/299 R

*Primary Examiner*—John Niebling
*Assistant Examiner*—John Starsiak Jr.
*Attorney, Agent, or Firm*—Townsend and Townsend and Crew LLP

[57] ABSTRACT

The phenomenon of electroendosmosis which occurs in electrophoretic separations and interferes with the efficiency, accuracy and reproducibility of the separations, is suppressed by the inclusion in the separation medium of a dissolved hydrophilic polymer which has been modified by amine groups covalently bonded thereto, in a controlled proportion relative to the polymer. This modified polymer suppresses electroendosmosis in both flee zone electrophoresis and molecular sieve electrophoresis. When this modified polymer is used in a capillary, the reduction which it produces in the electroendosmosis is the same as that achieved by coating the capillary wall with a neutral polymer.

24 Claims, 5 Drawing Sheets

SUPPRESSION OF ELECTROENDOSMOSIS DURING ELECTROPHORESIS IN GEL-FREE POLYMER MEDIA BY USE OF CHARGED POLYMERS

CROSS REFERENCE TO RELATED APPLICATION

This application is a continuation-in-part of co-pending application No. 08/136,689, filed Oct. 14, 1993, now abandoned.

This invention lies in the field of electrophoresis, and particularly electrophoresis through gel-free liquid media. The concern of this invention is the spontaneous occurrence of electroendosmosis and its detrimental effect on resolution and reproducibility in electrophoretic separations.

BACKGROUND OF THE INVENTION

Electroendosmosis, also referred to as electroendosmotic or electroosmotic flow, is a phenomenon which frequently occurs in electrophoretic separations of solute ions dissolved in a solvent or solvent system. Electroendosmosis is particularly pronounced in electrophoresis which is performed in capillaries made of a silica-containing material. Electroendosmosis causes bulk flow of the solvent system in response to the electric field, independently of the electrophoretic migration of the solute ions themselves which occurs at rates varying with the charge-to-mass ratio and the polarity of each ion. The bulk flow impairs the separation of solutes since it causes mobilization of all solutes at a common rate as part of the solution in which they are dissolved, thereby adding a nondifferentiating component to their mobility. This effectively shortens the path of travel attributable to electrophoresis itself, thereby lessening the degree of eleetrophoretic separation for a column of given length. In extreme cases, electroendosmosis causes peak broadening and loss of resolution. Electroendosmosis also impairs the reproducibility of a separation when repeated runs are performed in the same cell, column or capillary, since small amounts of solutes retained after the separation is terminated tend to alter the electroendosmotic effect, and the degree to which solutes retained from one separation affect subsequent separations depends on the balance between retention of the solutes within, and their release from, the separation region.

Until now, it has been believed that electroendosmosis arises solely from an electrokinetic potential existing between a solid surface such as the surface of a capillary wall or the surface of a bead in a packed bed and the liquid phase adjacent to the solid surface. As a result, electroendosmosis in capillaries is commonly suppressed by a coating on the interior capillary surface. The coating generally consists of neutral or charged groups covalently bound to the capillary surface, eliminating charged groups which were otherwise exposed on the surface and shielding the liquid medium adjacent to the wall from charged groups located near the surface which are not directly bonded to the coating material. Coatings are not an ideal means of eliminating electroendosmosis, however, since electroendosmosis develops in coated capillaries as well after repeated use. This is presumed to be attributable to a deterioration of the coating upon extended use or upon exposure to harsh solutes or separation media, or to the adsorption of charged analytes from previous experiments. The deterioration limits the useful life of a coated capillary. When capillaries with partially deteriorated coatings are used in isoelectric focusing, for example, the deterioration limits the length of the focusing time for any single run.

Another method which has been used to reduce electroendosmosis in capillaries is the inclusion of a small quantity of a cellulose derivative in the separation medium to raise the viscosity of the medium. This unfortunately affects the rate of migration of the solutes as well, and merely retards rather than eliminates the electroendosmotic effect.

A still further method is the application of highly charged hydrophobic polymers to coat the wall of the capillary prior to application of the samples, as disclosed by Wiktorowicz, U.S. Pat. No. 5,181,999, issued Jan. 26, 1993. Polymers such as Polybrene (N,N,N',N'-tetramethyl-1,6-hexanediamine polymer with 1,3-dibromopropane) have been used for this purpose. These polymers must be tightly bound to the wall, however, and the capillary must be pre-equilibrated with the separation electrolyte before the separation is performed. With protein analytes, it is important that the binding and equilibration be conducted prior to the introduction of the sample, to avoid having any residual Polybrene enter the analyte solution where uncontrollable interactions of the proteins with residual Polybrene will occur.

SUMMARY OF THE INVENTION

It has now been discovered that when electrophoresis is performed in certain liquid-phase separation media, electroendosmosis arises from the separation medium itself. These media are aqueous solutions of hydrophilic water-soluble polymers, including those disclosed in U.S. Pat. No. 5,089,111, issued Feb. 19, 1992, which is incorporated herein by reference. The disclosure in U.S. Pat. No. 5,089,111 is the separation of sample ions, particularly biomolecules, on the basis of molecular size by electrophoresis through an aqueous solution of a non-crosslinked polymer, in which the polymer contributes a molecular sieving effect to the separation. The molecular weight of the polymer is within or close to the molecular weight range of the sample ions to be separated, with the result that the migration of the sample ions through the solution is inhibited by the dissolved polymer to varying degrees.

This discovery arises from the observation that electroendosmosis in such systems can be reduced, and in some cases eliminated entirely, by the derivatization of the polymer with amines. Preferred derivatizations are those which result in the attachment of quaternary amine groups to the polymer chain. Attachment of amines or amine groups is preferably through covalent bonds, using linking groups if necessary. For hydrophilic polymers containing exposed hydroxyl groups, the linking groups and hence the quaternary amine groups may be attached at the locus of the hydroxyl oxygen.

In accordance with this discovery, the suppression effect is achieved by amine-derivatized polymer chains in which the density of amine groups on the derivatized chain, i.e., the number of equivalents of amine per 100 grams of the chain on which the mines are attached, is about 0.05 or above. Expressed alternately as a percent charge, defined as the mole percent of charged monomers used in the formation of a derivatized polymer chain relative to the total of all monomers, charged and uncharged, in the derivatized chain, the suppression effect is observed at a percent charge of about 5% or above.

These derivatized polymer chains can be used either by themselves or as a mixture with non-derivatized polymer chains, i.e., polymer chains to which no mine groups have been attached. Surprisingly, when derivatized chains and non-derivatized chains are mixed together, the beneficial effect of the derivatized polymer chains in suppressing electroendosmosis is not altered by dilution with the non-derivatized polymer, nor by increasing the concentration of the derivatized polymer, and test results indicate that the beneficial effect is attributable to a high degree of amine derivatization in the derivatized chains, which degree of derivatization has a distinct upper and lower limit, rather than to the total number of mine groups in the polymer mixture. No reversal of EOF was observed at any degree of substitution. At degrees of substitution exceeding the upper limit, the EOF was observed to increase in the same direction as for a fused silica capillary containing no derivatizes polymer, i.e., anode to cathode.

A particularly surprising aspect of this discovery is that the use of dissolved hydrophilic polymers which have been derivatized in the manner described above reduces electroendosmosis in a capillary to the same extent as the use of an internal surface coating on the capillary. Since the influence of the coating would be presumed to be one which is localized at the wall, it is entirely unexpected that a comparable effect is achieved in an uncoated capillary by a molecular modification of the separation medium whose influence is in the bulk of the separation medium rather than at the wall.

A related discovery, which is a further aspect of this invention, is that electroendosmosis arising from the electric double layer at the wall of the enclosure is also suppressed by the addition of a polymer derivatized with amines. Thus, in separations in which the concentration of dissolved polymer is too low to serve as a molecular sieving medium for solutes, the charge on the polymer still reduces or eliminates the electroendosmotic effect.

The and other features, qualifies and advantages of the invention are explained in detail below.

BRIEF DESCRIPTION OF THE DRAWINGS

In FIG. 2a, electrophoresis is suppressed by derivatization of a portion of the dextran with triethanolamine, whereas in FIG. 2b, electrophoresis is suppressed by a polyaerylamide coating on the inner capillary wall.

In FIG. 3a, a portion of the HMC has been derivatized with triethanolamine, whereas in FIG. 3b, underivatized HMC is used with a capillary whose inner wall has been coated with polyacrylamide.

In FIG. 4a, a low concentration of dextran derivatized with triethanolamine is used in an uncoated capillary, whereas in FIG. 4b, polymer-free buffer is used with a capillary whose inner wall has been coated with polyacrylamide.

DETAILED DESCRIPTION OF THE INVENTION AND PREFERRED EMBODIMENTS

Figure 1:
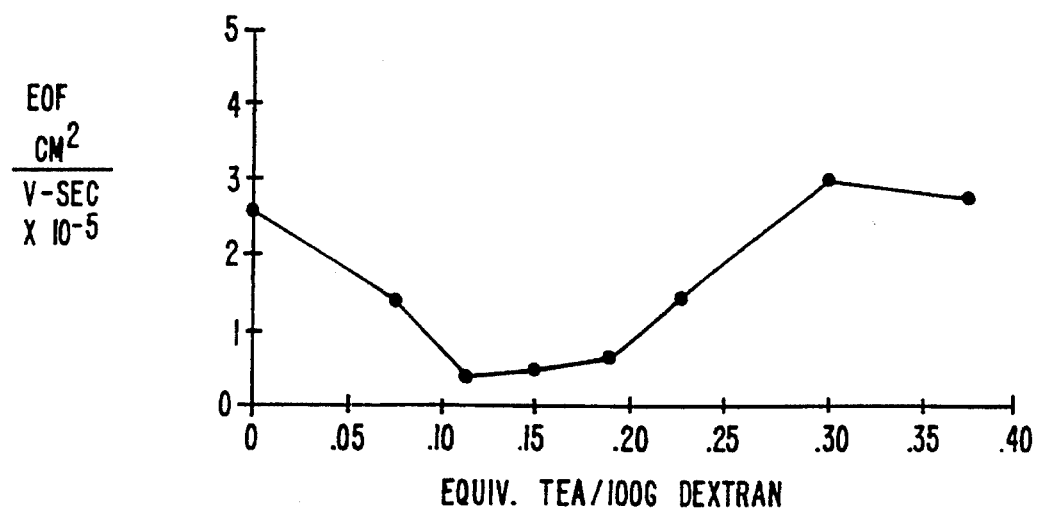
FIG. 1 is a plot of electroendosmotic flow in a fused silica capillary with an aqueous dextran solution as the separation medium, vs. the degree of derivatization of the dextran with triethanolamine.

This invention resides in the use of a hydrophilic polymer to which quaternary amine groups have been bonded as a separation medium in electrophoresis. Any of a variety of quaternary amine groups may be used, provided that the attachment of these groups does not result in precipitation of either the polymer or the solutes to be separated in the medium. Hydroxy-substituted amines, particularly di- or tri-(hydroxyalkyl)amines, are examples of such amines. The most preferred among these is triethanolamine.

Attachment of the quaternary amine groups to the polymer may be achieved by any conventional means resulting in the formation of a covalent bond. For polymers with exposed hydroxy groups, the hydroxy groups may be convened to ether linkages, for example, using conventional chemistry. Other conversions will be readily apparent to those skilled in this type of chemistry. The linking group joining the polymer to the quaternary amine group can be an alkyl bridge, an ether bridge, an ester bridge or a bridge which is a combination of these types. A preferred linking agent is allyl glycidyl ether. Appropriate coupling methods are well known among those skilled in synthetic chemistry.

The degree of derivatization is determined by the density of the quaternary amine groups throughout the polymer, or in the case of polymers where derivatization is through linkage at exposed hydroxyl groups, the number of such hydroxyl groups to which the quaternary amine groups have been attached through ether linkages. The degree of derivatization may be controlled by using a limited, i.e., less than stoichiometric, amount of linking reagent, amine, or both, the proportion of the amount used relative to the stoichiometric amount being equal to the desired degree of derivatization. The range of the degree of derivatization for purposes of the present invention is from about 1% to about 20% on a weight basis, and preferably from about 2% to about 10%. Expressed in terms of equivalents of amine per 100 grams of underivatized polymer, a preferred range is about 0.05 to about 0.25, with about 0.10 to about 0.20 as the most preferred range.

The degree of derivatization can also be expressed in terms of a percent charge, defined as the mole percent of charged monomers relative to the total of all monomers, charged and uncharged, present in the derivatized polymer. For purposes of the present invention, the percent charge is about 5% or above, preferably from about 5% to about 50%, and most preferably from about 15% to about 40%.

Examples of polymers suitable for use in this invention are cellulose derivatives, saccharide-based and substituted saccharide-based polymers, polysilanes, polyacrylamide, polyvinylalcohol and polyvinylpyrrolidone. Examples of cellulose derivatives are sodium carboxymethyl cellulose, sodium carboxymethyl 2-hydroxyethyl cellulose, 2-hydroxyethyl cellulose, 2-hydroxypropyl cellulose, methyl cellulose, hydroxypropyl methyl cellulose, hydroxyethyl methyl cellulose, hydroxybutyl methyl cellulose, and hydroxyethyl ethyl cellulose. Examples of saccharide-based and substituted saccharide-based polymers, both linear and branched, are dextran, hyaluronic acid (a polymer of acetyl-glucosamine and glucuronic acid as alternating units), locust-bean gum (a polysaccharide plant mucilage which is essentially galactomannan), Polytran (a seleroglucan available from Pillsbury Co., Minneapolis, Minn.), Pustulan (a polysaccharide available from Calbiochem Corp., San Diego, Calif.), carrageenan (a charged polysaccharide), guar gum (a neutral polysaccharide), pectin (a polyuronide consisting chiefly of partially methoxylated galactouronic acids joined in long chains), amylose, amylopectin, soluble starch and hydroxypropyl starch. Polymers of particular interest are methyl cellulose, hydroxypropylmethyl cellulose, hydroxyethylmethyl cellulose, hydroxybutylmethyl cellulose, dextran and agarose. The most preferred polymers are hydroxypropylmethyl cellulose and dextran.

When non-derivatized polymer is included in the separation medium for the separation of the sample ions by a molecular sieving effect, selection of the polymer is generally made in accordance with achieving the optimal separation, and will vary with the particular ions in the sample mixture. The molecular weight of the polymer is of primary interest in making this selection. Polymers varying widely in molecular weight may be used. Resolution of the sample ions will generally improve, however, as the polymer molecular weight approaches the range of the molecular weights of the sample ions. The best results are obtained with polymers having an average molecular weight which is between the lowest and highest molecular weights of the sample ions, and in particular with polymers whose molecular weight range covers (i.e., is at least coextensive with) the molecular weight range of the sample ions. In preferred embodiments, the polymer has an average molecular weight which is from about 10,000 to about 2,000,000, and within about 0.1 to about 200 times, more preferably from about 0.2 to about 20 times, and most preferably from about 0.5 to about 2 times the average (or suspected average) molecular weight of the sample ions.

These molecular weight considerations are application to the amine-derivatized polymer as well. Thus, whether the derivatized polymer is the sole polymer present in the separation medium, or whether it is present in a mixture with non-derivatized polymer, the derivatized polymer preferably has a molecular weight which is from about 10,000 to about 2,000,000, and within about 0.1 to about 200 times, more preferably from about 0.2 to about 20 times, and most preferably from about 0.5 to about 2 times the average (or suspected average) molecular weight of the sample ions.

Certain polymers are most conveniently characterized in terms of the viscosity of aqueous solutions in which the polymers are dissolved at specified concentrations and temperature. Cellulose derivatives, for example, are commonly characterized in this manner. While the value of this viscosity characterization may vary widely, best results with cellulose derivatives are generally obtained with those which are characterized as producing viscosities ranging from about 15 centipoise to about 17,000 centipoise when dissolved in water at 2 weight percent measured at 25° C., although in the context of this invention they would be used at other concentrations. Polymers such as these are useful in separating polynucleotides with chains ranging from about 10 to about 10,000 base pairs. Preferred cellulose derivatives are those which have viscosities of from about 1,000 to about 10,000 centipoise when prepared as 2% aqueous solutions measured at 25° C. It is to be understood that these viscosity characterizations are intended merely as an indication of the molecular weight of the polymer, and not of the actual viscosity when used in the context of the present invention.

Mixtures of polymers in which varying molecular weights are purposely combined may also be used. This will be particularly useful in separating sample mixtures which have a wide range of molecular weights, thus providing separation over the entire range.

The quantity or concentration of dissolved polymer in the separation medium may vary widely. When non-derivatized polymer is included for its molecular sieving effect, an effective quantity will be any quantity which improves the separation of the analytes to such varying degrees that electrophoretic separation on the basis of molecular size or charge-to-mass ratio is achieved. This will vary with various parameters of the system, including the column configuration and length, the presence and effect of other factors influencing the separation such as charge and electrophoretic mobility, the molecular structure, intrinsic viscosity and interactive character of the polymer itself, and the range of, and differences between, the molecular weights of the sample ions. The degree to which the retention times for the sample ions should be extended for best results will vary with the sample composition and the polymer being used. For separations of macromolecular species, increases in retention time of at least about 25%, preferably at least about 35%, and most preferably at least about 50%, will provide the best results. Preferred concentrations of nonderivatized polymer are about 0.05% or greater, more preferably from about 0.1% to about 30%, and most preferably from about 1% to about 20%, all percents on a weight basis.

The quantity of amine-derivatized polymer can also vary. Best results are often obtained at polymer concentrations of about 0.05% or greater, with a preferred range of about 0.1% to about 10%, and a most preferred range of about 0.1% to about 5%, all on a weight basis.

To conduct the separations in accordance with the present invention, equipment, materials, operating conditions and procedures used in conventional electrophoretic separations, including appropriately selected buffer systems, may be used. The invention is of particular utility in high performance electrophoresis as performed in capillaries, and particularly in capillaries of silica-containing materials such as fused silica. Preferred capillaries are those having internal diameters of less than about 200 microns, and most preferably about 10 microns to about 100 microns. The invention is also applicable to electrophoretic separations performed in slab-shaped cells and other non-capillary systems. For capillary systems, voltages of at least about 50 volts per centimeter length of the capillary are preferred, with a voltage range of about 100 volts/cm to about 1000 volts/cm particularly preferred.

The following examples are offered strictly for purposes of illustration, and are intended neither to define nor to limit the invention in any manner.

EXAMPLE 1

Preparation of Triethanolamine-DexWan
(TEA-Dextran)

A. Conversion of Dextran to Allyl Dextran

A solution was prepared by dissolving 10 g of dextran (molecular weight 2,000,000) in 100 mL of water. To the solution was added sodium tetrahydridoborate (10 mL of a stable aqueous solution at 4.4 M concentration in 14 M NaOH). The resulting mixture was heated to 70° C. with stirring, and 10 mL of allyl glycidyl ether was added with continued stirring. The temperature rose rapidly to 80° C., at which point heating was discontinued, and stirring was continued at room temperature for one hour. The solution was then transferred to a dialysis tube having a molecular weight cut-off of 12–14,000, and dialysis was performed against flowing deionized water for 14 hours to bring the pH to less than or equal to 7.0.

B. Conversion of Allyl Dextran to Dextran Bromide

The product of the preceding section was transferred to a 500 mL beaker, and 200 µL of $Br_2$ was added with stirring, which was continued until all droplets of $Br_2$ had disappeared.

C. Conversion of Dextran Bromide to TEA-Dextran

To the dextran bromide solution of the preceding section was added triethanolamine (2 g), with stirring. The mixture was then placed in a constant temperature bath at 65° C. where it was maintained for 4 hours with continuous stirring. The mixture was then dialyzed in a dialysis tube with a 12–14,000 molecular weight cut-off against flowing deionized water for 14 hours to bring the pH to 7.0 or less. The resulting mixture was filtered through No. 4 filter paper, and stored at 4° C. Based on the amount of bromine consumed in Part B of this example, and confirmation by total nitrogen determination, it was determined that the percent charge, i.e., the average mole percent of TEA-substituted monomers in the dextran chains relative to the total of all glucose monomers, substituted and unsubstituted, in the chains, was 25–30%.

EXAMPLE 2

Preparation of Triethanolamine-Hydroxypropylmethylcellulose (TEA-HMC)

The procedure of Example 1 was again followed, with a 2% (by weight) solution of hydroxypropylmethylcellulose at a viscosity of 4000 centipoise. Other modifications were the addition of 5 mL of isopropanol in the derivatization of the polymer with allyl glycidyl ether, and the use of $Br_2$-saturated water in place of pure $Br_2$, the $Br_2$-saturated water added until the solution began to turn yellow. The product was triethanolaminehydroxypropylmethylcellulose (TEA-HMC). Here as well, it was determined that the percent charge, i.e., the average mole percent of TEA-substituted monomers in the dextran chains relative to the total of all monomers in the HMC chains was 25–30%.

EXAMPLE 3

Electroendosmotic Flow Measurements in TEA-Dextran

This example illustrates the effect of adding TEA-dextran to a dextran solution to suppress or reduce the electroendosmotic flow which otherwise occurs in the dextran solution.

Four aqueous solutions were prepared, all containing 0.4 N TRIS-borate at pH 8.3. Two of these solutions further included 0.1% sodium dodecyl sulfate (SDS). One of the SDS-containing solutions and one of the solutions not containing SDS further included 8% (weight basis) dextran of molecular weight 2,000,000. The remaining two solutions further included 8% (weight basis) dextran of molecular weight 2,000,000 of which 5% was TEA-dextran as prepared in Example 1 above. The solutions were therefore as follows:

1. 0.4N TRIS-borate, SDS, dextran
2. 0.4N TRIS-borate, SDS, dextran+TEA-dextran
3. 0.4N TRIS-borate, (no SDS,) dextran
4. 0.4N TRIS-borate, (no SDS,) dextran+TEA-dextran The solutions were used in parallel experiments performed in capillaries of uncoated fused silica, each with an internal diameter of 50 microns and measuring 24 cm in total length. Niacinamide was used as a marker, at a concentration of 0.1 mg/mL, entering the capillary at the positive end. A voltage of 15 kV was impressed across the capillary, and detection was performed by an in-line ultraviolet light detector. The distance traveled by the marker from its entry end to the detector was 4.6 cm.

The time T (in minutes) required for the marker to reach the detector was measured. This value was then combined with the total length of the capillary ($L_t$= 24 cm), the length up to the detector ($L_e$=4.6 cm), and the applied voltage (V=15 kV), to determine the electroendosmotic flow (EOF, in units of $cm^2$/V-sec), according to the following formula:

$$EOF = \frac{L_t \times L_e}{V \times 60 \times T}$$

The values of EOF for each of the four runs are listed in Table I.

TABLE I

| | Electroendosmotic flow (EOF) ($cm^2$/V-sec) | |
|---|---|---|
| | Dextran Alone | Dextran plus TEA-Dextran |
| With SDS: | 3.7 | 0.4 |
| Without SDS: | 5.4 | 0.51 |

These results indicate that electroendosmotic flow is eliminated or at least sharply reduced, both in the presence of and in the absence of SDS.

EXAMPLE 4

Electrophoresis in TEA-Dextran at Varying Amounts of TEA

This example illustrates the relationship between the degree of derivatization of dextran by triethanolamine and the degree to which electroendosmotic flow is suppressed.

A series of runs was performed in accordance with the procedure of Example 3 above, using the same materials except that the proportion of quaternary triethanolamine groups relative to the total amount of dextran was varied. The results in terms of values for the EOF vs. the degree of derivatization are shown in FIG. 1. These results confirm those of Example 3 above that electroendosmosis is significantly and substantially suppressed by the quaternary triethanolamine groups, and further indicate that maximum suppression occurs within a range of 0.1 to 0.2 equivalents of TEA per 100 grams of dextran.

EXAMPLE 5

Electrophoresis in TEA-Dextran vs. Coated Capillary

This example reports the results of electrophoretic separations performed in fused silica capillaries, comparing an uncoated fused silica capillary containing an aqueous separation medium in which both dextran and TEA-dextran were dissolved, with a coated fused silica capillary containing an aqueous separation medium in which dextran was the only dissolved polymer.

A fused silica capillary was coated by treating the capillary surface with vinyl trichlorosilane and copolymerizing the silanized surface with linear polyacrylamide, according to the method disclosed in Hjertén, S., U.S. Pat. No. 4,680,201, issued Jul. 14, 1987. This capillary and a second fused silica capillary which had not been coated were each filled with a solution of 0.4N TRIS-borate, pH 8.3, 0.1% SDS, and 8% dextran (2,000,000 molecular weight). The dextran used in the solution for the uncoated capillary included TEA-dextran as prepared in Example 1, in an amount of 5% based on total dextran.

A standard mixture of eight SDS-treated proteins was used as a sample for each capillary. The proteins and their molecular weights were as follows:

lysozyme 14,400 trypsin inhibitor 21,500 carbonic anhydrase 31,000 ovalbumin 45,000 serum albumin 66,200 phosphorylase 97,400

β-galactosidase 116,200 myosin 200,000

The capillaries measured 24 cm in length and 50 microns in internal diameter, and the arrangement of Example 3 was used, with electrophoretic migration occurring toward the positive electrode, detecting at 220 nm. The samples were loaded electrophoretically at 10 kV for 8 seconds, and separation was performed at 15 kV.

Figure 2A:
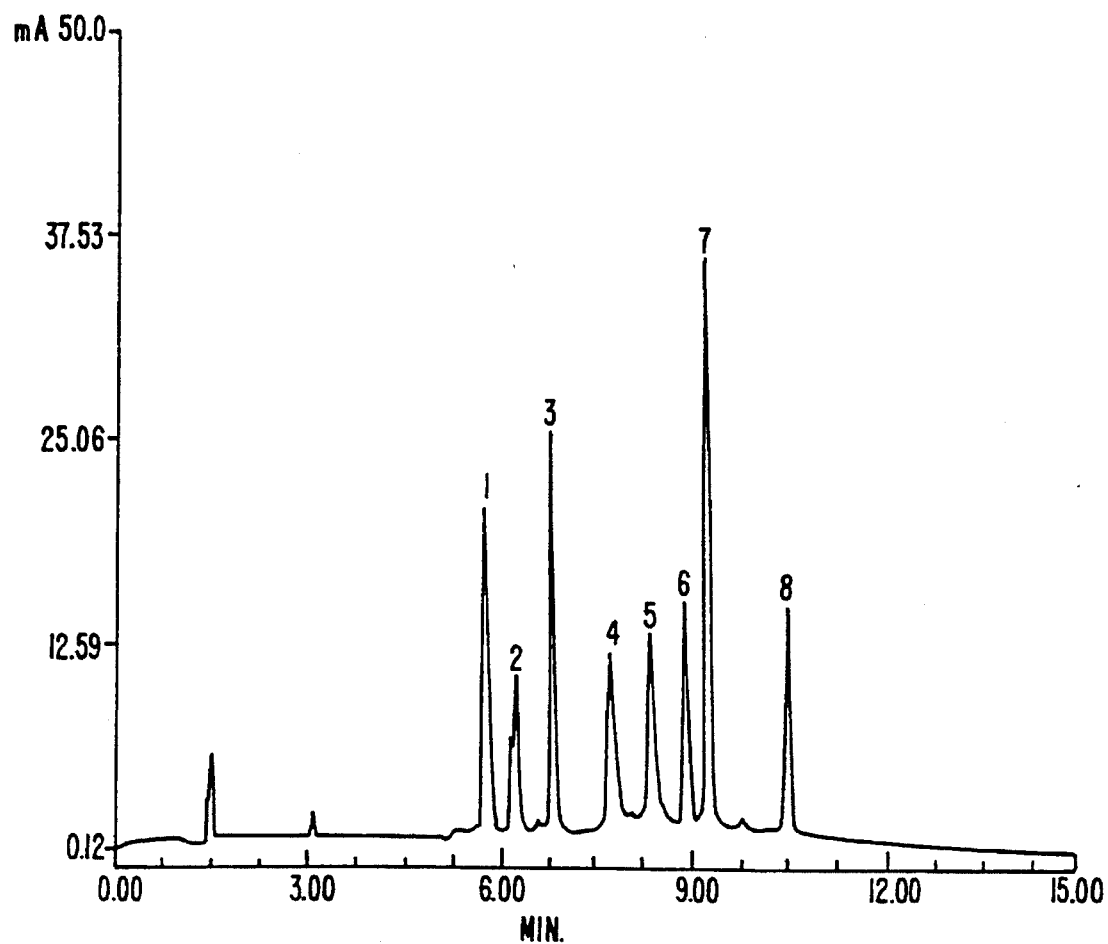
FIGS. 2a and 2b are detector traces representing electrophoretic separations of a standard mixture of eight SDS-treated proteins in a fused silica capillary using a dextran solution as the separation medium.
Figure 2B:
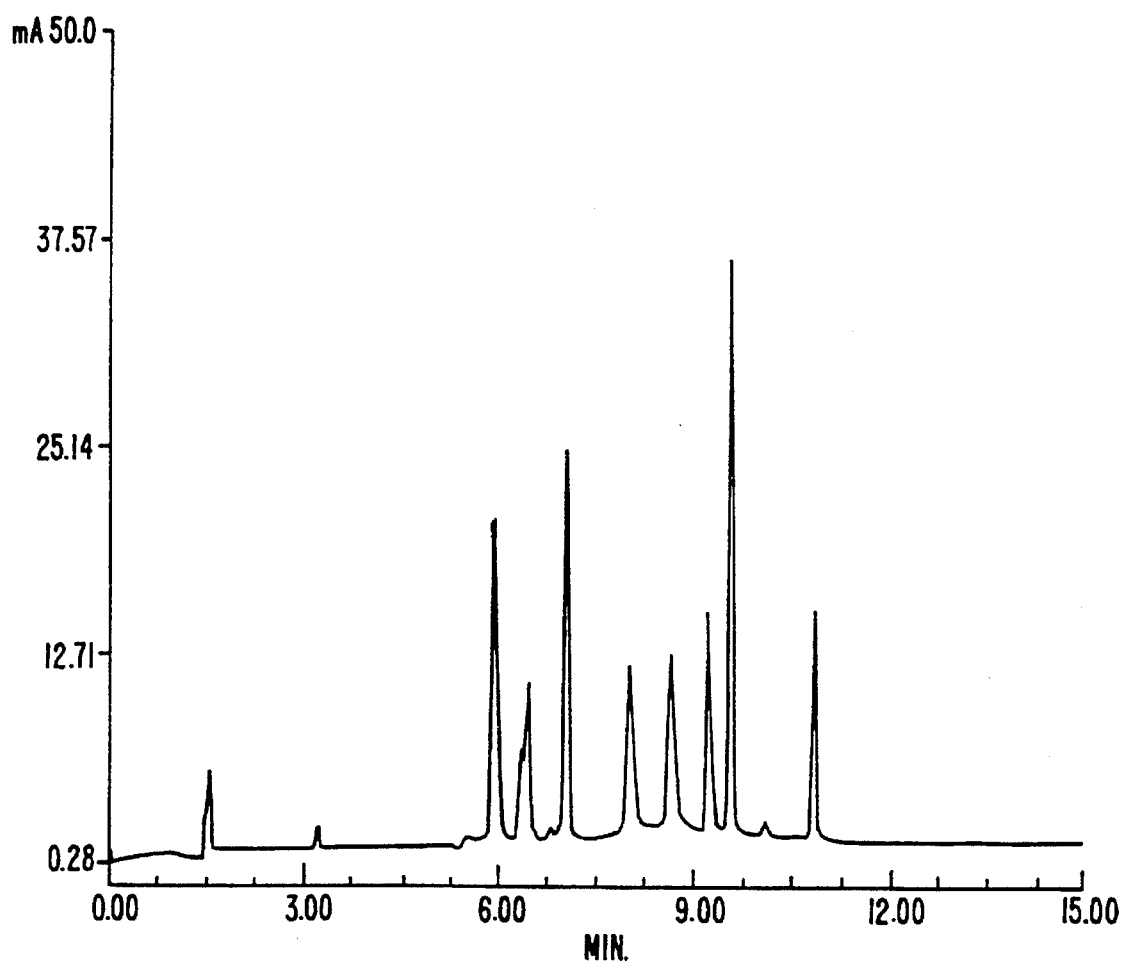

The detector trace for the separation in the uncoated capillary where TEA-dextran was included in the separation medium is shown in FIG. 2a, while the trace for the separation in the coated capillary where the separation medium contained only underivatized dextran is shown in FIG. 2b. The two traces are substantially identical, indicating that the TEA groups on the dextran suppressed electro-endosmotic flow to the same degree as the coating on the fused silica capillary.

EXAMPLE 6

Electrophoresis in TEA-HMC vs. Coated Capillary

This example offers a comparison similar to that of Example 5, except that TEA-hydroxypropylmethylcellulose as prepared in Example 2 was compared to underivatized hydroxypropylmethylcellulose.

A coated fused silica capillary was prepared in the same manner as that of Example 5, and the separation media were aqueous solutions of 0.3N TRIS-borate FI)TA at pH 8.3 and 0.5% hydroxypropylmethylcellulose. The hydroxypropylmethylcellulose used in the solution for the uncoated capillary included TEA-hydroxypropylmethylcellulose, in an amount of 5% based on total hydroxypropylmethylcellulose.

The sample mixture was an Ava II/Eco RI restriction digest of the plasmid pBR322, the digest consisting of nine fragments varying in length from 88 to 1,746 base pairs. The capillaries measured 50 cm in length and 24 microns in internal diameter, and the arrangement of Example 4 was again used, with detection occurring at 260 nm. The samples were loaded electrophoretically at 10 kV for 8 seconds, and separation was performed at 8 kV.

Figure 3A:
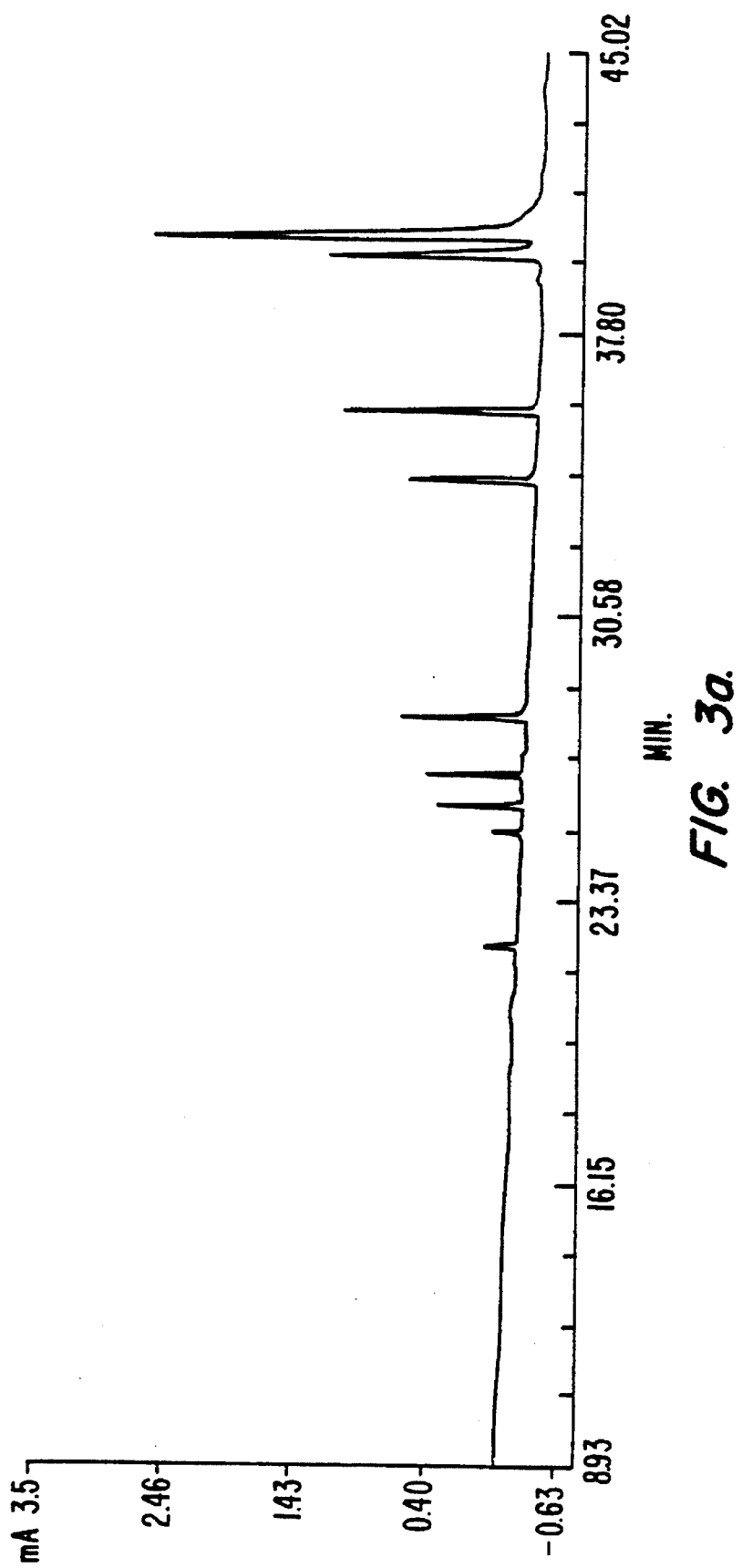
FIGS. 3a and 3b are detector traces representing electrophoretic separations of an Ava H/Eco RI restriction digest of pBR322 in a fused silica capillary using a hydroxypropyl-methyl cellulose solution as the separation medium.
Figure 3B:
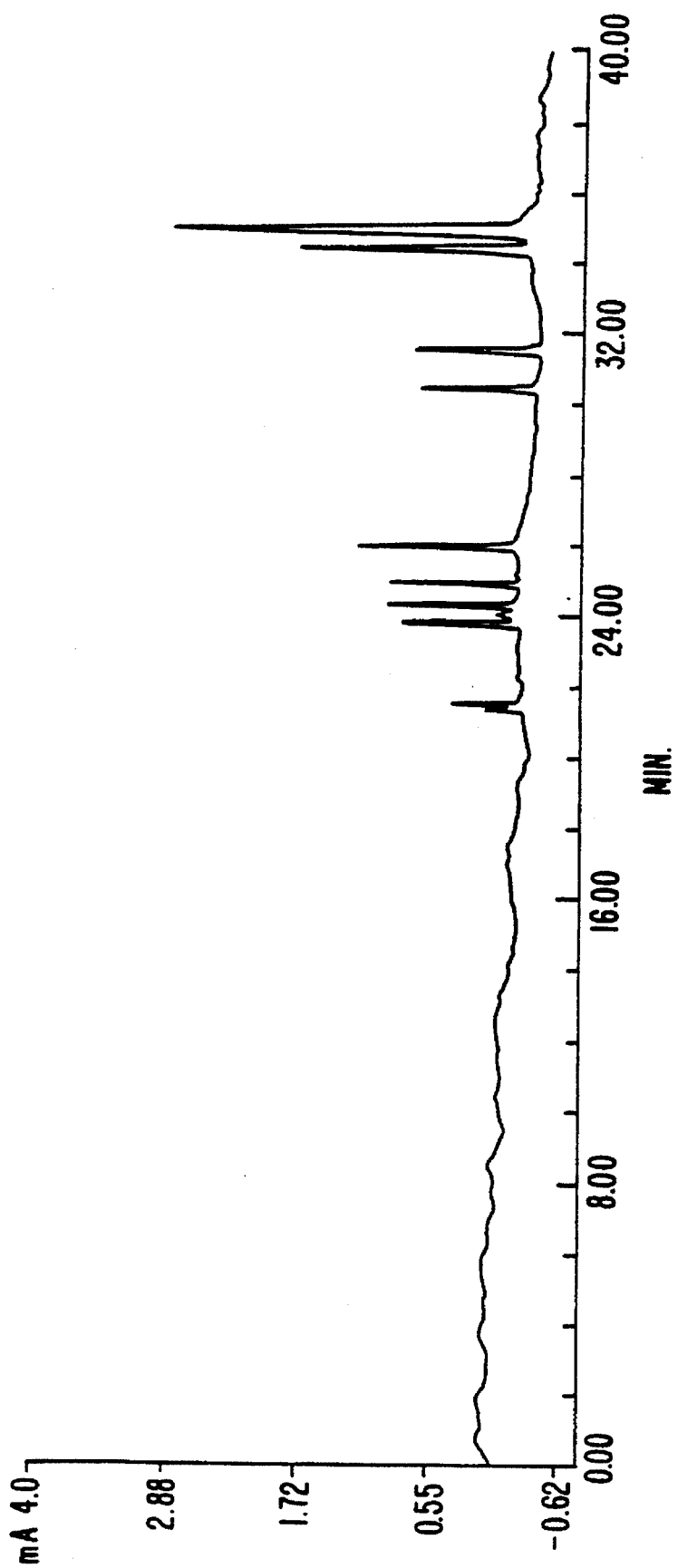

The detector trace for the separation in the uncoated capillary where TEA-HMC was included in the separation medium is shown in FIG. 3a, while the trace for the separation in the coated capillary where the separation medium contained only underivatized HMC is shown in HG. 3b. The two traces are substantially identical, indicating that the TEA groups on the HMC suppressed electroendosmotic flow to the same degree as the coating on the fused silica capillary.

EXAMPLE 7

Electrophoresis in TEA-Dextran vs. Coated Capillary With No Polymer

This example reports the results of electrophoretic separation with a charged polymer in the separation medium but at a concentration below the range at which molecular sieving occurs. Electrophoresis in an untreated capillary with a charged polymer dissolved in the buffer solution at a low concentration is compared with electrophoresis in a treated capillary which contains no polymer at all in the buffer solution.

Human transferrin is a protein existing in human serum, with a molecular weight of about 80,000 and an isoelectric point in the range of pH 5.0–6.0. Human transferrin occurs in various glycosylated forms which can be separated by capillary electrophoresis. Usually, a capillary coated with a linear polymer is used as the separation column.

A fused silica capillary measuring 24 cm in length and 50 μ in diameter was coated in the manner described in Example 5 above and filled with phosphate buffer at pH 8.0, without any polymer dissolved in the buffer. A second fused silica capillary of the same dimensions was left uncoated, and filled with the same buffer but further containing 0.4% by weight of a polymer consisting entirely of TEA-dextran as prepared in Example 1 above. A mixture of the various forms of glycosylated human transferrin was applied to each capillary, and the runs were performed with a voltage difference of 15 kV.

Figure 4A:
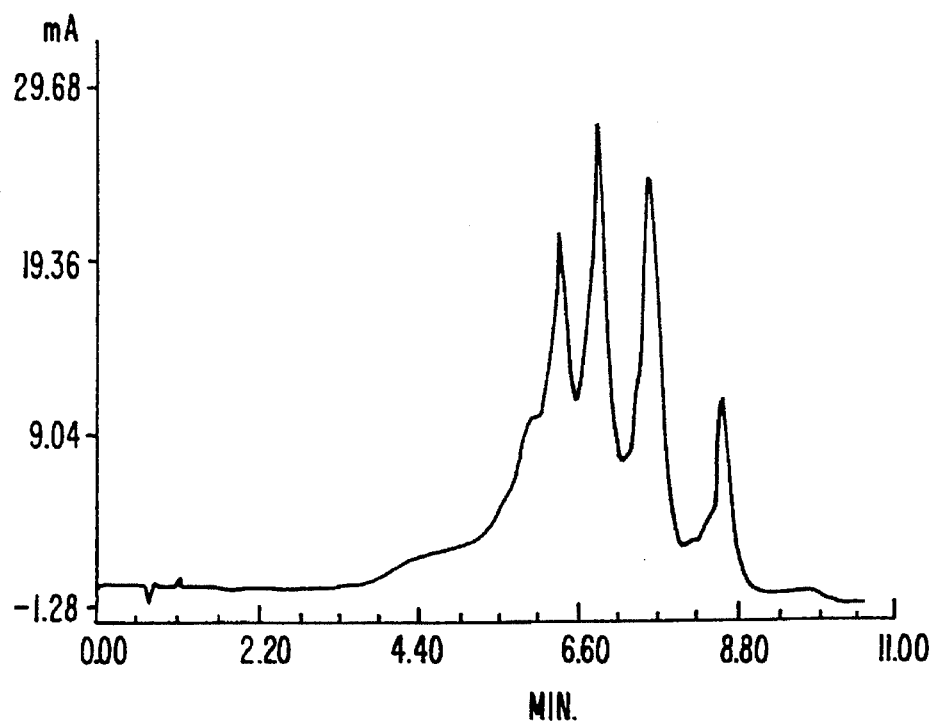
FIGS. 4a and 4b are detector traces representing electrophoretic separations of a mixture of glycosylated forms of human transferrin in a fused silica capillary under conditions of free zone electrophoresis without molecular sieving.
Figure 4B:
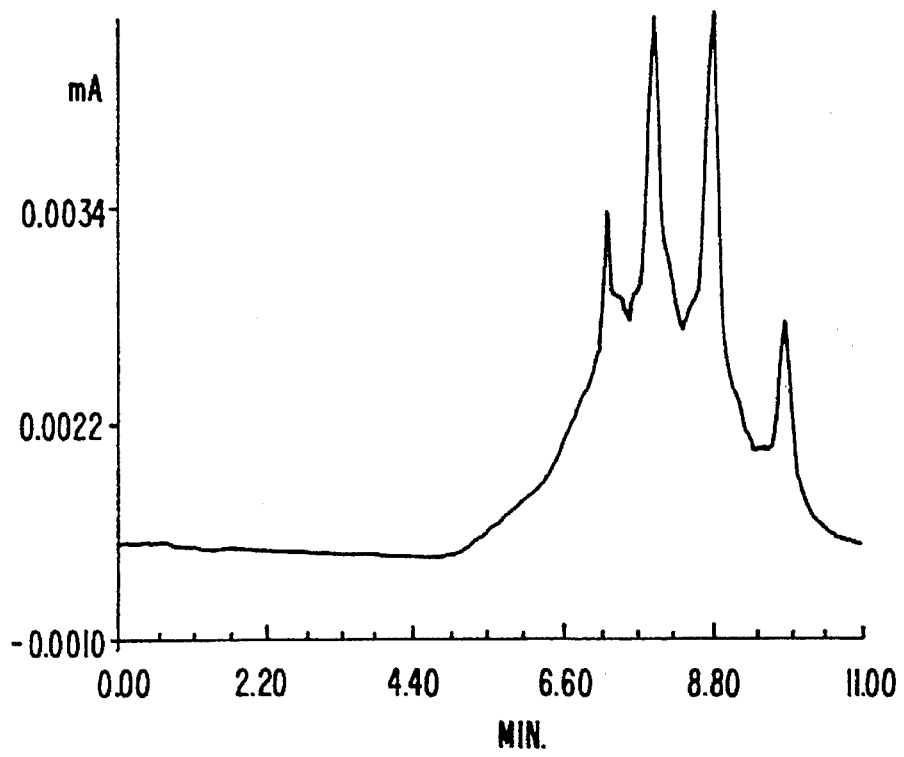

The detector trace for the separation in the untreated capillary with the charged polymer as an additive is shown in FIG. 4a while the trace for the separation in the coated capillary without any polymer is shown in FIG. 4b. The two traces are substantially identical, indicating that in this non-sieving mode as well, the charged polymer suppressed electroendosmosis to the same degree as the coated capillary and the separation occurred strictly by way of free zone electrophoresis.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method of suppressing electroendosmotic flow in an electrophoretic separation of a mixture of sample ions in a separation medium consisting essentially of a gel-free aqueous solution, said method comprising including in said gel-free aqueous solution a hydrophilic polymer derivatized by the bonding thereto of an amine at about 0.05 or more equivalents of amine per 100 grams of said polymer.

2. A method in accordance with claim 1 in which said derivatized hydrophilic polymer includes amine-bonded monomers at a mole percent of at least about 5% relative to the total of all monomers of said derivatized hydrophilic polymer.

3. A method in accordance with claim 1 in which said hydrophilic polymer is a member selected from the group consisting of cellulose derivatives, saccharide-based and substituted saccharide-based polymers, polysilanes, polyacrylamides, polyvinylalcohol and polyvinylpyrrolidone.

4. A method in accordance with claim 1 in which said polymer is derivatized to a degree of from about 0.05 to about 0.25 equivalents of amine per 100 grams of said polymer.

5. A method in accordance with claim 1 in which the concentration of said polymer in said gel-free aqueous solution is from about 0.1% to about 10% by weight.

6. A method in accordance with claim 1 in which said polymer is the sole polymer dissolved in said gel-free aqueous solution.

7. A method in accordance with claim 6 in which said non-amine-derivatized hydrophilic polymer has an average molecular weight which is within a range of about 0.2 to about 20 times the average of the lowest and highest molecular weights of said sample ions.

8. A method in accordance with claim 1 in which further dissolved in said gel-free aqueous solution is a non-amine-derivatized hydrophilic polymer at a concentration of about 0.05% by weight or greater.

9. A method in accordance with claim 8 in which the concentration of said non-amine-derivatized hydrophilic polymer is from about 0.1% to about 30% by weight.

10. A method in accordance with claim 8 in which said non-amine-derivatized hydrophilic polymer has an average molecular weight which is within a range of about 0.2 to about 20 times the average of the lowest and highest molecular weights of said sample ions.

11. A method in accordance with claim 1 in which said amine is bonded to said polymer as a quaternary amine group.

12. A method in accordance with claim 11 in which said quaternary amine group is a quaternary triethanolamine group.

13. A method in accordance with claim 1 in which said amine is bonded to said polymer through a linking group derived from allyl glycidyl ether.

14. A method in accordance with claim 11 in which said quaternary amine group is a quaternary triethanolamine group joined to said polymer through a linking group derived from allyl glycidyl ether.

15. A method in accordance with claim 1 in which said polymer is a member selected from the group consisting of methyl cellulose, hydroxypropylmethyl cellulose, hydroxyethylmethyl cellulose, hydroxybutylmethyl cellulose, dextran and agarose.

16. A method in accordance with claim 1 in which said gel-free aqueous solution is contained in a capillary having an internal diameter of less than about 200 microns.

17. A method in accordance with claim 16 in which said mixture is electrophoretically passed through said capillary by applying a voltage of at least about 50 volts per centimeter of capillary length across said capillary.

18. A method of suppressing electroendosmotic flow in an electrophoretic separation of a mixture of sample ions in a separation medium consisting essentially of a gel-free aqueous solution, said method comprising including in said gel-free aqueous solution a hydrophilic polymer derivatized by the bonding thereto of a hydroxy-substituted amine at about 0.05 or more equivalents of amine per 100 grams of said polymer.

19. A method in accordance with claim 18 in which said hydroxy-substituted amine is a member selected from di- and tri-(hydroxyalkyl)amines.

20. A method in accordance with claim 18 in which said hydroxy-substituted amine is a tri-(hydroxyalkyl)amine.

21. A method in accordance with claim 18 in which said derivatized hydrophilic polymer includes hydroxy-substituted amine-bonded monomers at a mole percent of at least about 5% relative to the total of all monomers of said derivatized hydrophilic polymer.

22. A method in accordance with claim 18 in which said hydrophilic polymer is a member selected from the group consisting of cellulose derivatives, saccharide-based and substituted saccharide-based polymers, polysilanes, polyacrylamides, polyvinylalcohol and polyvinylpyrrolidone.

23. A method in accordance with claim 18 in which said polymer is derivatized to a degree of from about 0.05 to about 0.25 equivalents of hydroxy-substituted amine per 100 grams of said polymer.

24. A method in accordance with claim 18 in which the concentration of said polymer in said gel-free aqueous solution is from about 0.1% to about 10% by weight.

* * * * *